United States Patent [19]

Conboy et al.

[11] Patent Number: 5,094,815
[45] Date of Patent: Mar. 10, 1992

[54] PHOTOLYTIC INTERFACE FOR HPLC-CHEMILUMINESCENCE DETECTION OF NON VOLATILE N-NITROSO COMPOUNDS

[75] Inventors: James J. Conboy; Joseph H. Hotchkiss, both of Ithaca, N.Y.

[73] Assignee: Cornell Research Foundation, Inc., Ithaca, N.Y.

[21] Appl. No.: 195,923

[22] Filed: May 18, 1988

[51] Int. Cl.⁵ .......................... G01N 21/76
[52] U.S. Cl. .................... 422/52; 422/68.1; 422/70; 422/82
[58] Field of Search .............. 422/52, 68.1, 70, 82; 436/107

[56] References Cited

U.S. PATENT DOCUMENTS

| | | | |
|---|---|---|---|
| 3,967,933 | 7/1976 | Etess et al. | 422/52 |
| 3,973,910 | 8/1976 | Fine | 23/230 PC |
| 3,996,002 | 12/1976 | Fine | 23/230 PC |
| 3,996,003 | 12/1976 | Fine et al. | 23/230 PC |
| 3,996,004 | 12/1976 | Fine et al. | 23/230 PC |
| 3,996,008 | 12/1976 | Fine et al. | 23/254 R |
| 3,996,009 | 12/1976 | Fine et al. | 23/254 R |
| 4,066,411 | 1/1978 | Fine et al. | 422/70 |
| 4,233,030 | 11/1980 | Twitchett et al. | 23/230 R |
| 4,303,419 | 12/1981 | Frank et al. | 422/82 |
| 4,335,073 | 6/1982 | Sherwood et al. | 422/52 |
| 4,822,564 | 4/1989 | Howard | 422/52 |
| 4,843,016 | 6/1989 | Fine | 422/52 |

OTHER PUBLICATIONS

Fine, D. H. et al, J. Chromatog., 107:351 (1975).
Sen, N. P. et al, Food Additives Contamin., 4:357 (1987).
Shuker, D. E., et al, Anal. Chem., 55:2152 (1983).
Fine, D. H. et al, In "The Relevance of N-nitro Compounds to Human Cancer"; Bartsch, H.; O'Neill, I.; Schulte-Hermann, R., Ed.; International Agency for Research on Cancer: Lyon, 1987; IARC Scientific Publication No. 84; p. 216.
Singer, G. M. et al, J. Chromatography, 133:59 (1977).
Sen, N. P. et al, In "N-nitro Compounds: Occurrence, Biological Effects and Relevance to Human CAncer"; O'Neill, I. K.; Von Borstel, R. C.; Miller, C. T.; Long, J.; Bartsch, H. Ed.; International Agency for Research on Cancer: Lyon, 1984; IARC Scientific Publication No. 57; p. 137.
Krull, I. S., et al, J. Anal. Toxicol., 5:42 (1981).
Weinkam, R. J. et al, Clin. Chem., 24:45 (1978).
Mirvish, S. S., et al, J. Agric. Food Chem., 28:1175 (1980).
Hotchkiss, J. J., Advances in Food Research, 31:54 (1987).
Hotchkiss, J. H. et al, J. Assoc. Office Anal. Chem., 64:1037 (1981).

Primary Examiner—Peter Kratz
Attorney, Agent, or Firm—Jones, Tullar & Cooper

[57] ABSTRACT

The invention relates to a photolytic interface and its use in series between a High Pressure Liquid Chromatograph (HPLC) and a chemiluminescence detector for the detection of trace (nanogram) amounts of N-nitroso compounds including N-nitrosamides and non-volatile N-nitrosamines in aqueous-based fluid samples. HPLC effluent containing separated N-nitrosoamino acids and N-nitrosoamino amides is introduced into a glass coil with a purge stream of He and irradiated with ultraviolet light. Nitric oxide cleaved by photolysis is rapidly separated from solvent through a series of cold traps and carried by the He into the reaction chamber of a chemiluminescence detector. Biological matrices, such as urine and gastric fluid, can be analyzed directly at high sensitivity without concentration and/or extraction.

7 Claims, 5 Drawing Sheets

PHOTOLYTIC INTERFACE FOR HPLC-CHEMILUMINESCENCE DETECTION OF NON VOLATILE N-NITROSO COMPOUNDS

This invention was made in part under NIH Grant No. 1 R01 CA 40833-03. The United States has certain rights to this invention.

BACKGROUND OF THE INVENTION

A majority of the over 300 tested N-nitroso compounds have been positive for carcinogenicity in laboratory animals (Preussmann, R. et al, "Chemical Carcinogens, Second Edition"; Searle, C. W., Ed.; American Chemical Society: Washington. D.C. 1984; American Chemical Society Monograph No. 182; Chapter 12). Humans are exposed to N-nitroso compounds from a variety of sources including foods, occupational exposures, cosmetics, and formation within the body. Certain N-nitrosamides are also widely used as therapeutic anticancer agents (Preussmann, R. et al, "Chemical Carcinogens, Second Edition"; Searle, C. W., Ed.; American Chemical Society: Washington, D.C., 1984; American Chemical Society Monograph No. 182; Chapter 13; Hotchkiss, J. H. Advances in Food Research 31,54 (1987)). For these reasons, there is considerable interest in the analysis of trace levels of these compounds in biological and environmental media.

Many N-nitrosamines can be analyzed, either directly or after derivatization, by gas chromatography coupled to a Thermal Energy Analyzer Detector (TEA; Hotchkiss, J. H. J. Assoc. Offic. Anal Chem., 64:1037 (1981)). The TEA is a modified chemiluminescence detector which relies on the thermal cleavage of the N-N bond producing a nitric oxide (NO) radical. The nitric oxide is reacted with ozone to produce an excited nitrogen dioxide which emits a photon upon decay (Fine, D. H. et al, J. Chromatog., 107:351 (1975)). The photons are detected and amplified by a photomultiplier tube. There are two limitations to this system; first is that the N-nitroso compounds must be volatile enough, or made volatile enough for gas chromatography, and secondly, they must yield nitric oxide upon thermolysis. N-Nitrosamides and related compounds, unlike N-nitrosamines, typically rearrange upon thermolysis to yield molecular nitrogen instead of nitric oxide and are only weakly detected by the TEA. In addition, several N-nitrosamines that are of interest are not suitable for gas chromatography. HPLC-TEA methods have been reported (Sen. N.P. et al, Food Additives Contamin., 4:357 (1987)) but mobile phases containing water give inconsistent results.

Shuker and Tannenbaum, Anal. Chem. 55:2152 (1983) have described a method in which N-nitrosamides are photolytically cleaved by uv irradiation. The resulting nitric oxide was oxidized to nitrite, and reacted post-column with Griess reagent to form a chromophore which was detected spectrophotometrically at 541 nm. Sensitivity was 6 to 100 ng as injected depending on the specific N-nitroso compound.

Fine et al, In "The Relevance of N-nitro Compounds to Human Cancer"; Bartsch, H.; O'Neill, I.; Schulte-Hermann, R., Ed.; International Agency For Research on Cancer: Lyon, 1987; IARC Scientific Publication No. 84; p. 216 have reportedly modified the pyrolysis chamber in a standard TEA in order that N-nitrosamides release nitric oxide during pyrolysis. Sensitivities (3:1; S:N) of less than 1 ng injected were reported for standards. Complete details of the instrument were not provided and the need for further development was noted. Singer et al, J. Chromatography, 133:59 (1977) used dilute acid to cleave N-nitrosamides and coupled the resulting nitrite to Griess reagent. A sensitivity of 50 to 100 ng was reported. Sen and Seaman. In "N-nitro Compounds: Occurrence, Biological Effects and Relevance to Human Cancer"; O'Neill, I. K.; Von Borstel, R. C.; Miller, C. T.; Long, J.; Bartsch, H., Ed.; International Agency for Research on Cancer: Lyon, 1984; IARC Scientific Publication No. 57; p. 137, have also chemically cleaved the nitroso group from N-nitroso compounds and have detected the nitric oxide by chemiluminescence using a modified TEA. The slow response time of the system caused considerable peak broadening. Detection of N-nitrosamides by uv (Krull, I. S., et al, J. Anal. Toxicol., 5:42 (1981)), MS after derivatization (Weinkam, R. J. et al, Clin. Chem., 24:45 (1978)), and denitrosation with subsequent detection of the amide (Mirvish, S. S. et al, J. Agric. Food Chem., 28:1175 (1980)) have also been proposed.

U.S. Pat. No. 4,233,030 to Twitchett et al teaches a photochemical reaction interposed between a high pressure liquid chromatograph column and a detector where the analysis is based on a constituent or a species resulting from irradiation. The property detected is either an increase or a decrease in fluorescence in compounds such as lysergic acid diethylamide (LSD) and cannabinol when subjected to visible or uv light absorbance. The property of the converted product that is analyzed is either enhanced light absorbance or reduced light absorbance.

The difficulty of analyzing N-nitroso compounds is noted by Fine et al in U.S. Pat Nos. 3,996,002; 3,996,003; 3,996,004; and 3,973,910, all of which are incorporated herein by reference to show both the problem faced and earlier attempts to solve it by interposing a "non catalytic pyrolysis" step between the liquid chromatograph and the detector means. U.S. Pat. No. 3,996,003 and 3,996.004 relate to the detection of NO and nitrate and nitrite respectively. U.S. Pat. No. 3,996,008 and 3,996,009 related to similar processes using a gas chromatograph. In U.S. Pat. No. 3,973,910 Fine converts the nitroso compounds to NO gas by the sole energizing step of heating at 200° C. to 300° C.

All of the above methods fail to satisfy the need for a highly selective, sensitive and simple process for the resolution, dection and analysis of N-nitroso compounds including N-nitrosamides and non-volatile N-nitrosamines in nanogram quantities. The present apparatus and methods fills such a need.

SUMMARY OF THE INVENTION

One object of the invention is a photolytic interface apparatus which allows radiation reactions to take place in a two-phase liquid/gas environment which allows selective nonvolatile components to be transformed to gaseous products which pass with the gas phase to a detector for analysis and detection of nanogram quantities at high resolution and specificity, wherein the gaseous products are correlatable with the said nonvolatile components.

Another object is an apparatus and process wherein the said interface is used in a system comprising a High Pressure Liquid Chromatograph and a Chemiluminescence detector.

A further object is an apparatus and system for detecting and analyzing trace amounts (nanogram) of N-nitrosoamides and other nonvolatile carcinogenic N-nitroso compounds directly and in biological and environmental samples.

Abbreviations of specific N-nitroso compounds referred to herein are as follows: NHPRO, N-nitrosohydroxyproline; NSAR, N-nitososarcosine; NMU, N-nitrosomethylurea; NPRO, N-nitrosoproline; NTHZCA, N-nitrosothiazolidine carboxylic acid; NEU, N-nitrosoethylurea; MNNG, N-methyl-N-nitro-N-nitroso-guanidine., NMTHZCA, N-nitrosomethylthiazolidine carboxylic acid.

Figure 8:
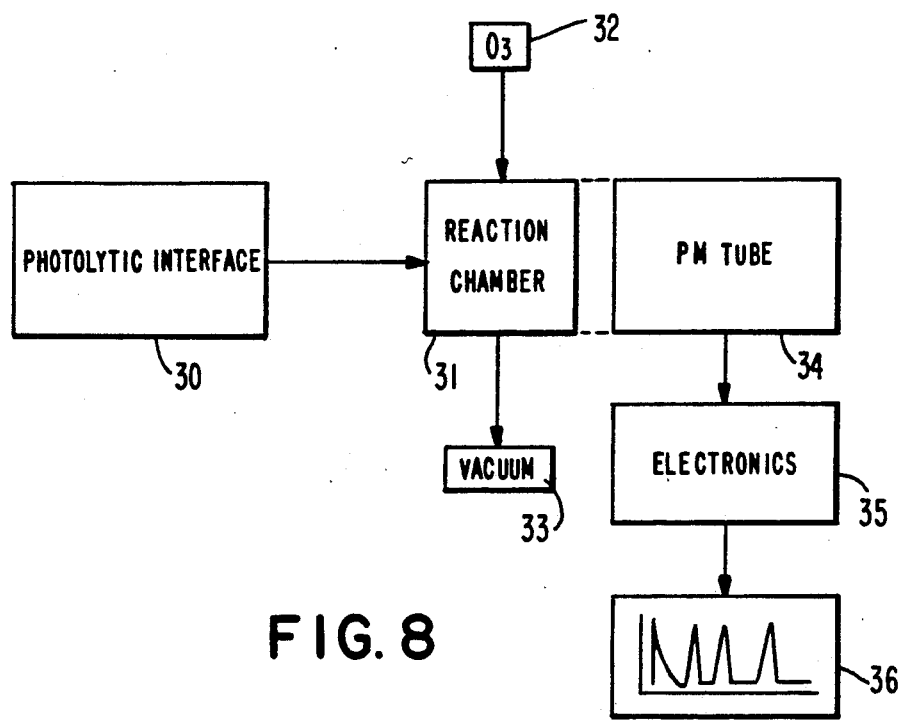

FIG. 8 is a block diagram showing the relationship of the photolytic interface in series with a chemiluminescence detector.

DETAILED DESCRIPTION OF THE INVENTION

The present invention relates to a photolytic interface apparatus for accepting liquid eluate from a high pressure liquid chromatograph which contains separated trace amounts of one or more compounds to be detected and analyzed and for converting the said compounds by non-pyrolytic means to a gaseous product which can be detected and analyzed with high selectivity and sensitivity in a detector adapted to detect said gaseous product which comprises:

a) a means for combining the liquid eluate with an inert gas to form a biphasic liquid/gas mixture and for conveying the mixture to a photolytic reactor;

b) a vertically positioned photolytic reactor tube for accepting the biphasic liquid/gas mixture and for irradiating in continuous flow the mixture at a specified radiant energy or range and a specified wattage, at a specified gas flow rate, and at specified liquid flow rate related to the internal tube diameter to produce a gaseous product corresponding to said trace compounds to be detected; said reactor positioned vertically to allow unobstructed continuous flow of liquid assisted by gravity at said specified flow rate;

c) a means for regulating the flow rate of the inert gas and the flow rate of the liquid;

d) a means for irradiating the liquid/gas mixture as it flows downwardly in the reaction tube at a specified radiation energy, a specified inert gas flow rate and a specified liquid flow rate;

e) a means for cooling the reactor tube to maintain the temperature within the reactor substantially below the temperature at which said compounds would pyrolyze or thermally degrade.

f) a means for separating other components of the liquid/gas mixture exiting the photolytic reactor from the gaseous product to be detected and analyzed and the inert gas.

The invention further relates to a process of identifying in an aqueous-based or mobile phase eluent sample from a high pressure liquid chromatograph column one or more components including N-nitroso compounds of a medication, biological fluid or environmental sample which comprises:

a) mixing said eluent with an inert gas to form a biphasic gas/liquid mixture;

b) reacting said mixture with ultraviolet radiation in the herein described photolytic interface apparatus under a specified gas flow rate and liquid flow rate in a small bore tube reactor whose inside diameter in millimeters is a multiple of from 0.5 to 2.0 times the liquid flow rate given in milliliters per minute to convert the said components to a detectable species corresponding to the amount of each component in the eluent sample; and c) detecting said detectable species in a detector.

Such processes are advantageous for the detection and analysis of compounds such as carcinogenic compounds and other compounds present in biological fluids including urine, blood, gastric juices and the like and aqueous extracts derived therefrom.

Another object of the invention is a process for analyzing and detecting in an aqueous based mobile phase sample one or more N-nitroso compounds having the formula:

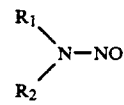

wherein R1 and R2 are the same or different organic radicals including those radicals which together with the non-nitroso nitrogen constitute a nitrogen heterocyclic radical, which comprises:

a) injecting the said aqueous based sample into a high pressure chromatograph to produce a liquid eluent where the nitroso compounds are resolved and separated;

b) mixing the liquid eluent with an inert gas to produce a biphasic gas/liquid mixture having a specified gas flow rate and a specified liquid flow rate;

c) passing the gas/liquid mixture through a photolytic interface to convert the said nitroso compounds to nitric oxide gas which exits said photolytic interface in an exit stream;

d) cooling said exit stream to substantially remove all liquid and solid components excepting the nitic oxide (NO) and inert gas;

e) detecting the NO gas by means of a chemiluminescence detector.

Standard Compounds

Caution: Nitroso compounds are potent animal carcinogens and must be handled with appropriate care. N-nitrosoamino acids were synthesized by the method of Keefer and Lijinsky, *Tetrahedron.* 26:5137 (1970) except for N-nitroso-4-methyl-thiazolidine carboxylic acid (NMTHZCA) which was graciously donated by H. Ohshima. N-Nitrosamides, except for N-nitrosotrimethyl urea (NTMU), were obtained from commercial sources and used without further purification. NTMU was synthesized by nitrosating trimethylurea (Alpha Chemical Co.) at pH 2.5 in the presence of acetic acid. HPLC analysis (254 nm) gave a single peak.

Chromatography

Both ion suppression (10 mM trifluoroacetic acid, pH<2) and ion pairing (2 mM tetrabutylammonium dihydrogenphosphate, pH=7) liquid chromatography were used to separate the N-nitroso compounds. Acetonitrile was used as an organic modifier with gradient elution as indicated (1 ml/min). Columns were Brownlee Polymer RP (10 cm×4.6 mm, 10 u particle size), self-packed silica (15 cm×4.6 mm. 5 u particle size), or a self-packed Spherisorb ODS (15 cm×4.6 mm, 5 u particle size, 12% loading). The Beckman HPLC system consisted of two 110B pumps, 421A controller, 210A injector and a 160 uv detector.

Photolysis Apparatus

Figure 1:
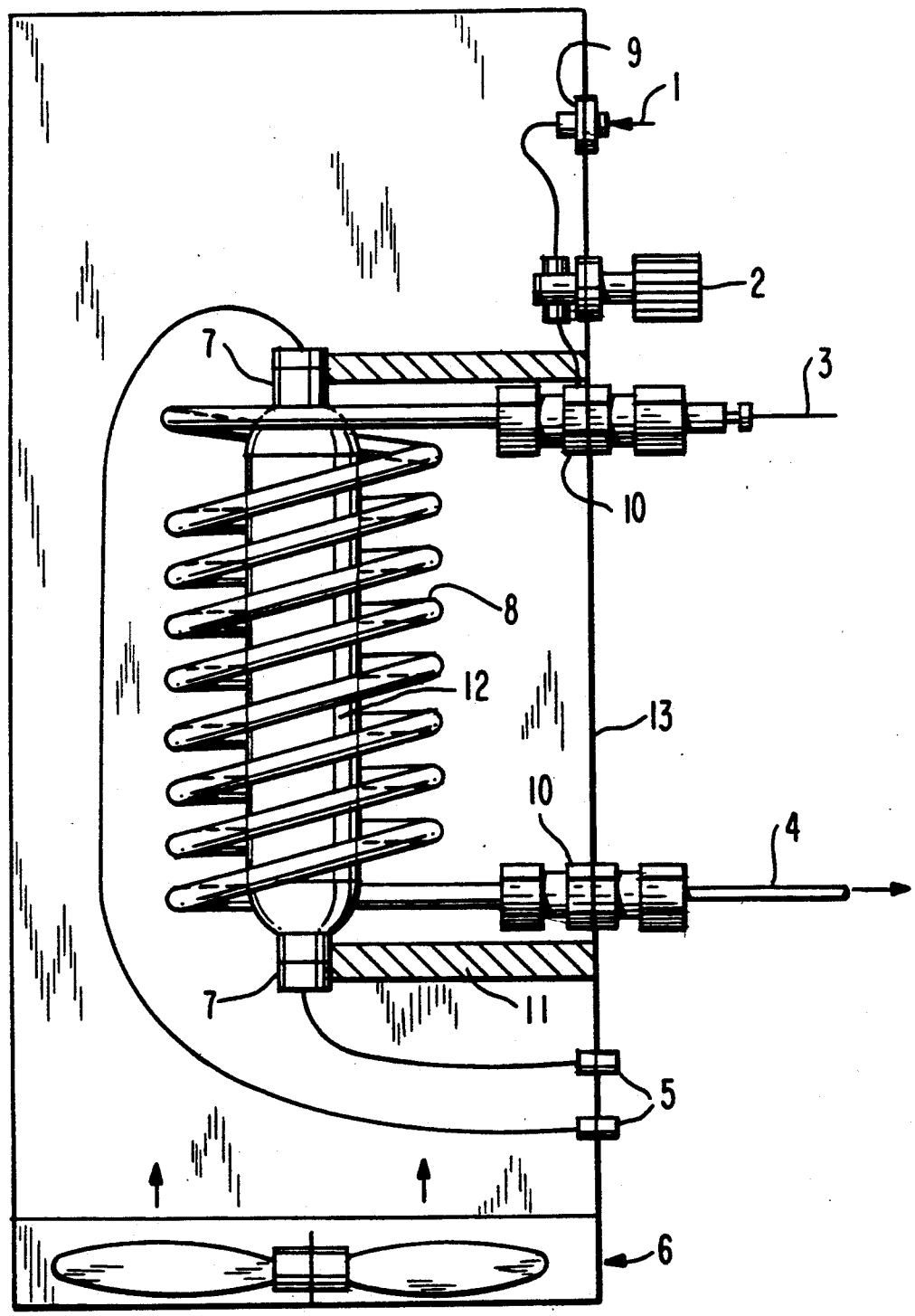
FIG. 1 is a side view drawing of the photolytic interface apparatus showing He inlet Δ 1; analyzer pressure adjustment (He flow rate) Δ 2; effluent from HPLC column Δ 3; 0.125 in. ss tubing from interface to traps and chemiluminescence detector Δ 4; electrical connectors to ballast circuit Δ 5; box fan Δ 6; 200 W lamp Δ 12; glass reactor coil Δ 8; 0.0625 in. bulkhead union Δ 9; 0.25 in. bulkhead unions Δ 10; Teflon support towers Δ 11.

The photolysis apparatus is detailed in FIG. 1. The effluent of the chromatographic column was transferred to the photolysis coil via a microbore ss tube 3 (0.013 mm i.d.×0.051 mm o.d.; Upchurch Scientific, Oak Harbor, Wash.). The end of the ss transfer line was fed into the photolysis coil 8 approximately 3 cm after passing through a 0.25 in. Swagelok bulkhead union 10 and a Swagelok 0.25 in.×0.0625 in. reducer. The 0.25 in. union was modified into a tee by silver soldering a 0.0625 in. o.d. ss tube into the side in order to mix the carrier gas with the column effluent. The photolysis coil 8 consisted of an 8 ft.×7 mm o.d.×1 mm i.d. borosilicate glass tube coiled to a diameter of 6 cm and a width of 12 cm. The carrier gas (He) was adjusted using a fine metering valve 2 (Nupro Model M-2MA) to give a total analyzer pressure of 1.7 to 2.0 torr with an oxygen pressure of 0.9 torr. A medium pressure mercury vapor lamp 12 (Model 679A-0360, Canrad-Hanovia, Newark, N.J., powered by a ballasted circuit 34245-101) was vertically mounted in the center of the photolysis coil 8 on Teflon towers 11. The entire photolysis apparatus was mounted inside an aluminum box 13 in which a cooling fan had been mounted in the bottom and several air holes had been drilled in the top. The outer surface of the photolysis coil was covered with heavy aluminum foil. The ballast was powered through a thermal safety circuit (Model HTLC1, Cannon Instrument Co., State College, Pa.) in order to prevent over heating in case of failure of the cooling fan 6. The temperature of the air leaving the box was 40–45 C.

Figure 7:
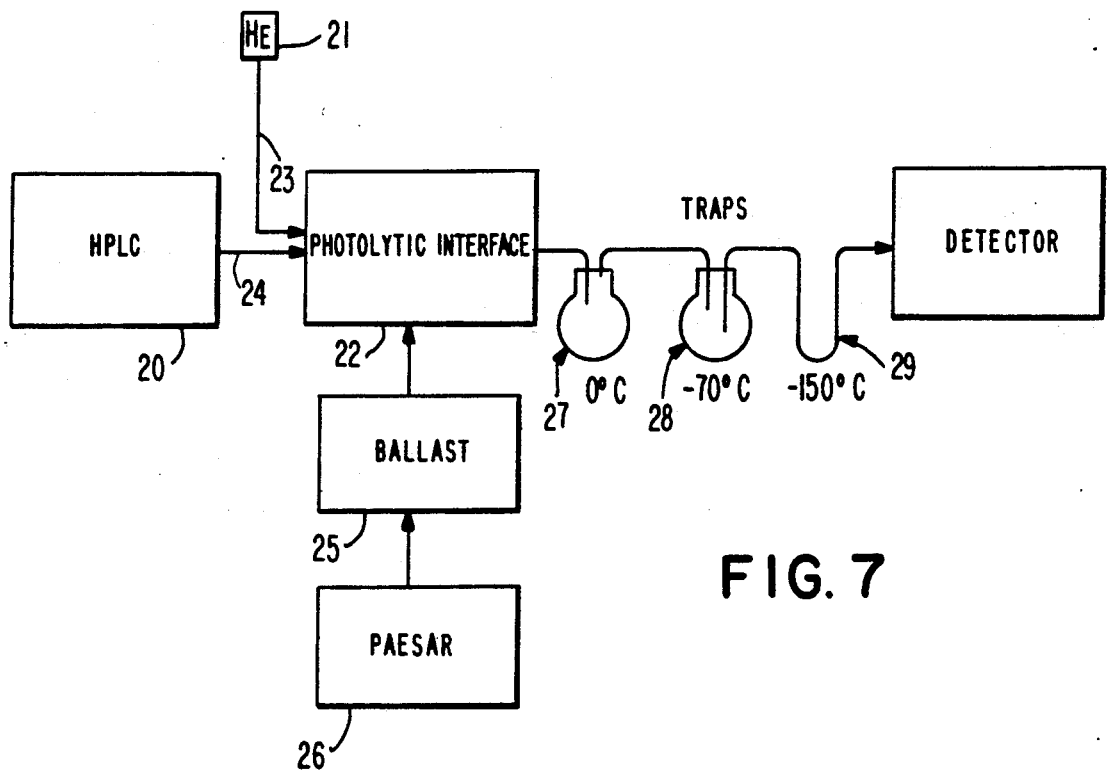
FIG. 7 is a block diagram of total apparatus system incorporating the photolytic interface between the High Pressure Liquid Chromatograph stage and the Chemiluminescence detector.

The effluent of the photolysis coil was directed through exit port 4 to a series of cold traps 27,28,29 by 0.125 o.d. ss tubing (See FIG. 7). The first trap 27 was a 100 ml round bottom flask in which the end of the inlet tube was located midway between the geometric center and the neck of the flask. The outlet tube was above the inlet tube. The second trap 28 was a 50 ml test tube where the inlet tube was at the top of the test tube and the outlet near the bottom in order to increase the capacity of the trap. Both traps were cooled in Dry Ice-acetone baths. The third trap 29 was a 0.25 o.d. ss U-tube cooled to $-159°$ C. with $LN_2$. The first 27 and second 28 traps were sealed with drilled teflon stoppers fitted with O-rings.

The nitric oxide produced in the photolysis coil 8 was detected using the chemiluminescence detector (FIG. 8) portion of a model 543 Thermal Energy Analyzer 31 (Thermedics, Woburn, Mass.) by bypassing the pyrolyzer portion of the instrument and directing the carrier gas directly into the reaction chamber. In some cases, the chromatographic column effluent was first directed through a uv detector in series with the photolysis coil.

N-Nitrosamines absorb in the region of 300 to 380 nm while N-nitrosamides absorb in the region of 380 to 430 nm. Borosilicate glass is transparent in these regions. The N-nitroso group will be cleaved in sufficient energy is absorbed and nitric oxide liberated (Chow, Y. L.; In "N-Nitrosamines"; Anselme, J. P., Ed.; American Chemical Society, Washington, D.C., 1979; American Chemical Society Symposium Series 101; p. 18). The nitric oxide is carried to the reaction chamber of the chemiluminescence detector by the helium carrier gas and reacted with ozone, thus producing the chemiluminescence reaction. However, the nitric oxide can be hydrolyzed by the mobile phase to give nitrite ($NO_2^-$), which is nonvolatile and not detected. It was, therefore, necessary to purge the HPLC effluent with helium as it passed through the photolysis coil so that the nitric oxide would be removed from the solution as it was formed. When the HPLC effluent was photolyzed prior to being mixed with the helium, only a very weak response was seen, presumably because the nitric oxide was oxidized to nitrite. The presence of both liquid and gas (helium) phases during photolysis is an important feature of the system.

Referring to the Chemiluminescence Detector, FIG. 8 shows the photolytic interface 30, ozone reaction chamber 31 with ozone source 32 and vacuum pump 33, photomultiplier tube 34, electric amplifier 35 and chart recorder 36.

Instrument Design

The 200 watt lamp 12 was utilized with an electronic device 26 (PAESAR, Lutron Electronics Co., Cooperburg, Pa.) which would continuously attenuate the wattage of the lamp between 120 and 200 watts. A wattage of 120 reduced the sensitivity of the detector by about 20% of that of the 200 watt lamp. Also tested was a 450 watt lamp (260 to 450 watts with the PAESAR). A wattage of 260 did not significantly reduce the response to N-nitrosamines compared to 450 watts, but 450 watts slightly reduced the response from N-nitrosamides, possibly due to thermal degradation at the higher operating temperature. The higher wattage lamp gave an unacceptably high baseline when urine and gastric juice samples were analyzed.

Several types of coils in which to irradiate the HPLC effluent were tested including several sizes and types of Teflon (TFE, FPA, FEP) microbore tubing with wall thicknesses of 0.006 to 0.016 in. Although the Teflon worked initially, a loss of response was noted after only 2–3 weeks of use. The response could not be recovered by washing the tubing and could only be recovered by replacing the tubing with virgin material. Others have also noted that Teflon can be degraded under intense uv irradiation (Batley Anal Chem. 56:2261). These problems were overcome by the use of the thick-walled glass capillary tubing. The tubing did require cleaning with chromic acid approximately every 2 weeks when heavily used for very dirty samples such as urine.

Glass tubes with lengths between 2 and 10 feet lengths were tested. Tubes of less than 8 feet gave a decreased response while longer than 10 foot tube foot lengths did not result in increased response. The inside diameter of the tubing was important for chromatographic resolution. Inside diameters of 2 mm required a solvent flow rate of at least 2 ml/min in order to produce acceptable peak shape. One mm i.d. tubing gave good peak shapes at a flow rate of 1 ml/min. The flow of solvent must be in the direction of gravity or the resulting solvent bumping within the coil (when used in a non-vertical position) resulted in pressure surges in the analyzer and an erratic base line. To achieve the proper selectivity and sensitivity the photolysis tube must be positioned vertically and have a continuing downward slope to maintain a downward flow of liquid assisted by gravity, to maintain distinct solid and liquid phase and to establish the required flow rates of both liquid and gas as noted in this application.

Various parameters of the photolytic interface reactor tube are critical for obtaining the high sensitivity and selectivity of product detection and analysis which distinguish the present invention and makes it superior over the prior art patents of Fine which depend mainly on the pyrolytic decomposition of the analyzed component such as N-nitroso compounds.

One parameter that is critical to the operation of the instant apparatus is the He gas flow rate and the liquid flow rate within the reaction chamber. These can be modified by the analyzer pressure adjustment (He flow rate) 2 shown in FIG. 1. When the He flow rate is too low (below 5 ml/min) relative to the liquid flow, the gaseous product bands corresponding to individual N-nitroso compounds will widen and overlap thus adversely affecting resolution, especially when more than one N-nitroso compound is present in the reactor. When the He flow is too high (>30 ml/min) relative to the liquid flow, the sensitivity is adversely affected due in part to the fact that the pressure in the analyzer will increase and the concentration of nitric oxide (NO) in the He will be decreased causing a diminished response. The flow rate of the mobile phase (liquid) moving downwardly in the vertical reactor tube, determined in part by gravity, in part by the HPLP pump setting, and in part by the flow rate of the He, is best maintained at a rate of 0.5 to 3.0 ml/minute and preferrably from 0.75 to 1.5 ml/minute and most preferrably at about 1 ml/minute for best sensitivity and selectivity.

Another important aspect of the invention is the addition of He gas to the liquid sample prior to the irradiation. Helium also establishes a gas phase under reduced pressure in the coil which enables the NO to be readily removed from the aqueous liquid to avoid reaction therewith. The He protects the nitric oxide (NO) formed from reaction with oxygen and other reactants present in the liquid or generated during the irradiation reaction. The inert gas thus establishes the gas phase, protects the NO generated and insures that it is carried intact to the detector.

Referring next to the reactor tubing, the inside tubing diameter, the outside diameter, composition and wall thickness are all important for obtaining high sensitivity and selectivity of the overall gaseous detection. The inside diameter should be from about 0.75 to about 1.25 mm with an O.D of $0.25 +/- 0.05$ inch. Preferred I.D. is 1.0 mm when the tube is glass. Most preferred reactor tubes are those made from borosilicate glass having a uv transparent window of from about 280 nm to about 430 nm. The length of the tube can vary within strict limits and will depend on the tube diameter and composition. For borosilicate glass of 1.0 mm I.D. a minimum length of about 10 feet is preferred. This length at the above described tube dimensions gives excellent sensitivity and selectivity. There is no advantage of having a tube length much in excess of ten feet. Shorter reactor tube lengths reduce the sensitivity of the product gas (NO) detection. Reactor tubes may be composed of other materials, such as Teflon, as long as the the radiation window is in the range indicated above. Borosilicate (Pyrex) glass is the preferred present reactor choice because it perform for a longer period and can easily be cleaned for continued use.

Another parameter that effects the operation of the apparatus is the internal pressure of the system. Although the addition of inert gas generally has an effect of increasing the internal pressure, the system is best operated under a vacuum of 1–2 mm mercury. This vacuum assists in the phase transfer of the gaseous product (NO) from liquid to gas in the detector mechanism. Such vacuum is best applied downside of the detector mechanism and assists in removal of products passing through the detector.

Another most important aspect of the invention is to maintain the reactor at a temperature of below 100° C. and preferably close to ambient temperature (below 50° C.) by protecting the reactor tube from excessive heat from the irradiation source. This is accomplished by a fan 6 as indicated in FIG. 1. In FIG. 1 the fan is shown postioned beneath the reactor tube radiation lamp; the actual position is not critical in itself so long as reactor tube cooling is effected.

Referring next to the irradiation source that effects the breakdown of the N-nitroso bonds to generate NO for detection in a chemiluminescence detector, like the reactor tube, the uv source is one that provide radiation of from about 190 to about 500 millimicrons with a preferred range of 280 to 430 millimicrons. As stated above the addition of He is important in removal of volatile product from the aqueous phase and protecting the volatile products (NO) in the gaseous phase. Other inert gases including argon can be used but He is the preferred gas for purposes of this invention. In order to properly control the output of the lamp, it should be powered by a ballasted circuit and operated at a constant amperage and voltage. The wattage of the lamp is controlled by a device capable of power attenuation such as a PAESAR (Lutron Company) controller. These items are represented as items 25 and 26 in block diagram of FIG. 7. It is important to control the energy of the lamp to prevent excessive interference.

One skilled in the art will recognize that the reactor and process can be adapted for the analysis of a variety of different chemical sustances and biological fluids other than those of the nitroso compounds illustrated in the best mode examples. For example, the reactor and process will be useful for C-nitroso compounds, nitramines, nitro compounds, nitrite esters, and other reactions and detections. Additionally contemplated are other methods for implementation of the basic idea of irradiating a 2-phase system for the purpose of removing a gaseous product for subsequent detection. One variant for example, is a system where both liquid and gas are dispersed by atomization, nebulization or aerosol generation to form very small droplets of liquid just prior to the irradiation step. It is anticipated that by spray atomization of the liquid eluate from the HPLC the predominant phase will be gas having liquid droplets. Thus the transfer of gaseous product from liquid to gas will be improved and that system will further enhance the sensitivity and selectivity of analysis of nonvolatile compounds. Other similar methods include nebulization and aerosol type mixing.

The following examples dealing with N-nitroso compounds and NO detection generally exemplify the improved photolytic interface and its use in high pressure liquid chromatography system. The invention should not be construed narrowly or restricted to these examples. One skilled in the art will appreciate that such two-phase irradiation reactor will also be useful in the analysis of trace amounts of a wide variety of nonvolatile compounds that under the influence of irradiation to produce a gas or other reaction product capable of being analyzed by chemiluminescence and/or other detector means. Unless otherwise indicated temperatures are given in degrees C, pressure in mmHg, wavelength in nanometers (nm), and liquid flow rates as ml/minute.

The following Examples are generally exemplary of the invention which should not be construed narrowly or limited to these conditions. It should be appreciated that in such two phase (liquid-gas) photolytic interface the irradiation may vary as well as the amount and form of liquid present in the gas phases. It is contemplated that an atomization of liquid to form small droplets of liquid in the He gas phase will be equally useful as well as other known means of liquid/gas components.

EXAMPLE 1

A 7 component standard containing 1, NHPRO; 2, NSAR; 3, NMU; 4, NPRO; 5, NTHZCA; 6, MNNG; 7, NMTHZCA was tested in the apparatus of the instant invention as described above and as illustrated in the block diagram of FIG. 7 using the following conditions: Column, Polymer RP; Mobile phase was A: 10 mM TFA, B: AN, gradient elution: 0% B to 7% B @ 1%/min. hold 5 min, then 7% B to 22% B @ 1.5%/min, hold 3 min, 20 ul injection, 20–100 ng/component, lamp power 260 W.

Figure 2:
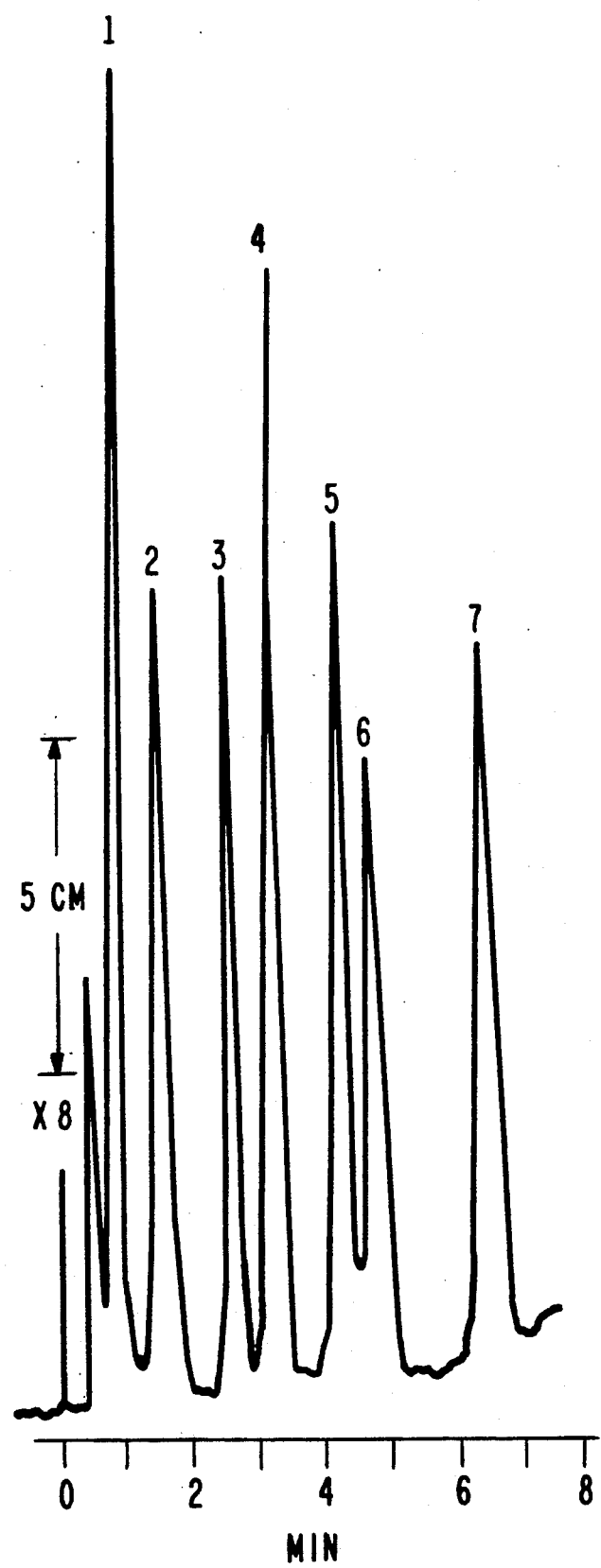
FIG. 2 is a chromatogram showing resolution of a component standard: NHPRO 1; NSAR 2; NMU 3; NPRO 4; NTHZCA 5; MNNG 6 and NMTHZCA 7.

As shown in FIG. 2, chromatogram excellent resolution of each nitroso compound was achieved.

EXAMPLE 2

Under the same apparatus and conditions as in Example 1 a mixed standard containing 1, NHPRO; 2, NSAR; 3, NMU; 4, NPRO; 5, NTHZCA; 6, NEU; 7, MNNG; 8, NMTHZCA was tested using both a chemiluminescence detection (A) and a 254 nm uv detector (B) in series. Column and gradient elution were the same as for Example 1 with 20 ul injection, 2.4 to 14 ng/component and lamp power 260 W. Results shown in FIG. 3 indicate superior selectivity and sensitivity for instant apparatus and process as opposed to inferior sensitivity and selectivity for the uv detector.

EXAMPLE 3

Figure 4:
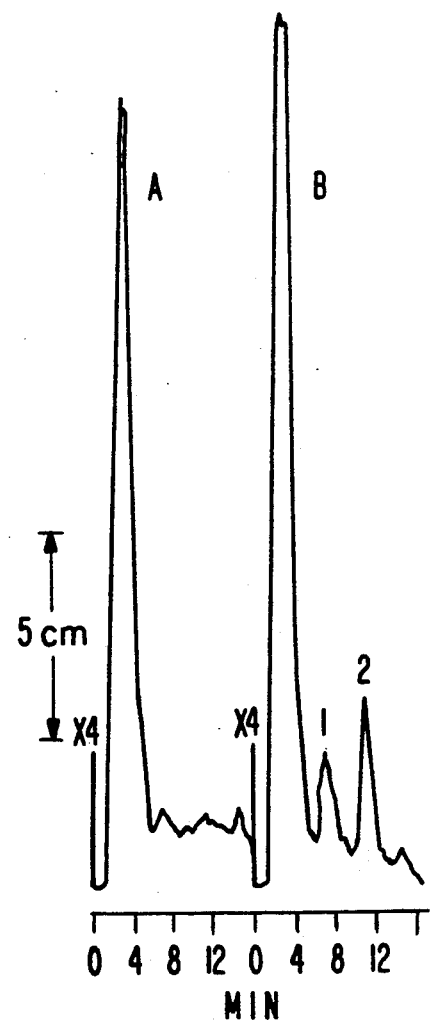
FIG. 4 is a chromatogram comparing 2,000 ul injections of unspiked human urine (A) with spiked human urine (B) having 7.5 and 8.0 pg/ul of NPRO 1 and NTHZCA 2.

In an experiment conducted in a manner similar to Example 1, samples injections of 2,000 ul of unspiked human urine (A) and spiked human urine (B) containing 7.5 and 8.0 pg/ul of NPRO (1) and NTHZCA (2) were run. Column and mobile phase were the same as in Example 1, with gradient elution 5% B, hold 2 min. increase to 20% B @ 3%/min and lamp power 120 W. Prior to injection the urine was passed at neutral pH through a C18 solid phase extraction tube (SPE) to remove neutral compounds, the eluent acidified and injected. The results are shown in FIG. 4 chromatogram. These tests indicate that biological samples such as urine may be used with little or no preparation in a mobile phase sample.

EXAMPLE 4

Figure 5:
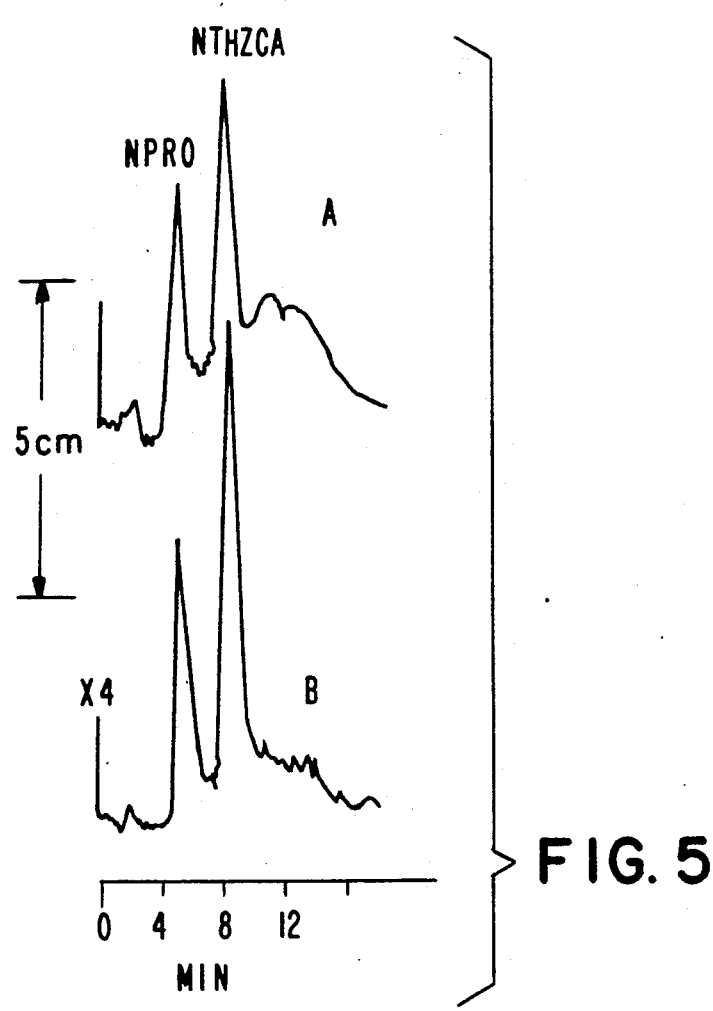
FIG. 5 is a chromatogram comparing 10 ml extract of human urine (A) that had been spiked with 7-8 ng/ml of NPRO and NTHZCA and standard solution (B) of 0.15-0.16 ng/ul of NPRO and NTHZCA.

In a variant of Example 3, an extract of 10 ml of human urine (A) that had been spiked with 7-8 ng/ml of NPRO and NTHZCA was tested and compared with a standard solution (B) of 0.15–0.16 ng/ul of NPRO and NTHZCA. Column and mobile phase were same as FIG. 2, gradient elution 5% B to 20% B @ 7.5%/min, 100 ul injection and lamp power 120 W. The extract was made by passage through a $C_{18}$ solid phase extraction tube at neutral pH to remove neutral components followed by ethylacelate extraction, evaporation to dryness and the residue was reconstituted in a minimum amount of aqueous mobile phase. Results shown in FIG. 5 show excellent resolution and identification of both NPRO and NTHZCA.

EXAMPLE 5

Figure 6:
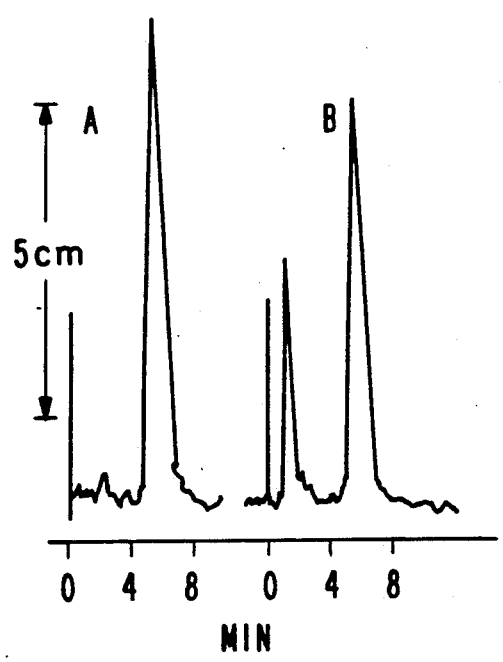
FIG. 6 is a chromatogram comparing standard solution of NTMU (A) and an extract of porcune gastric fluid (B) spiked with 42 ng/ml of NTMU.

In a variant of Example 4 an extract of porcine gastric fluid (B) that had been spiked with 42 ng/ml of NTMU was tested against a standard solution of NTMU (A) using 17 ng injection. The column was that used in FIG. 2 with isocratic elution with 15% AN/10 mM TFA, 20 ul injection and lamp power 120 W. The porcine gastric fluid was passed through a solid phase extraction (SPE) tube to retain the NTMU followed by an extraction of SPE with ethylacetate and treatment as in Example 4 prior to injection. Results shown in FIG. 6 show excellent detection of NTMU component in the spiked gastric fluid extract. These results show the excellent adaptability of the improved apparatus and method to gastric fluids and biological fluids in general.

Even though there is considerable dead volume in the system the peak shapes and widths for a standard mixture were quite satisfactory (FIG. 2). All seven components were eluted within 8 minutes with peak widths of 30 to 60 seconds. The relative response ratios for several N-nitrosoamino acids and N-nitrosamides are given in Table 1.

Figure 3:
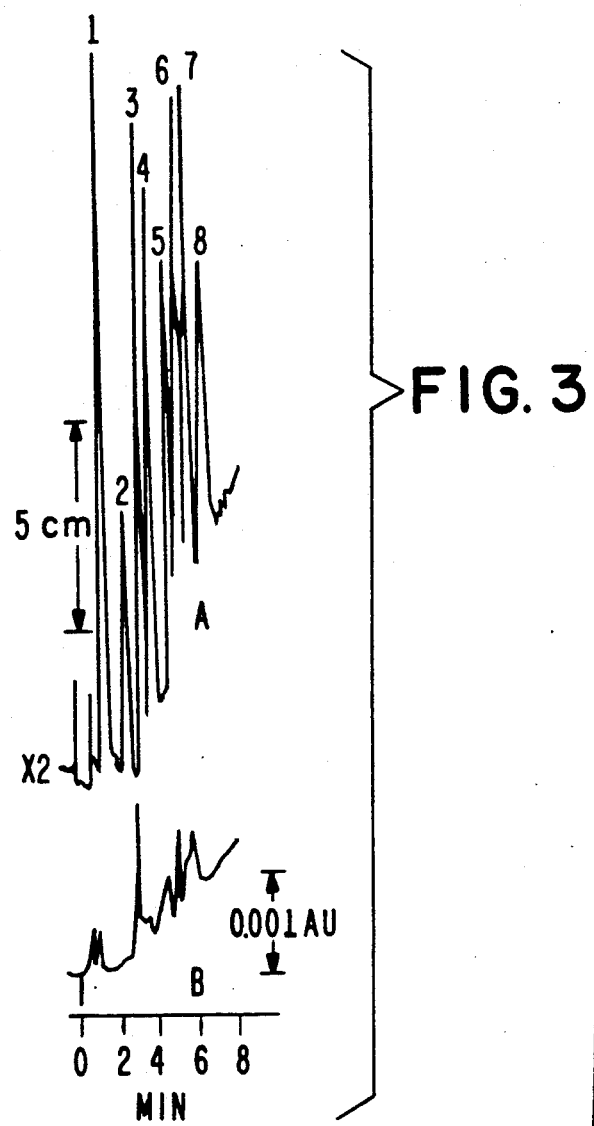
FIG. 3 is a chromatogram of chemiluminescence detection (A) and a 254 nm uv detector placed in series showing respective resolution of a mixed standard containing NHPRO 1; NSAR 2; NMU 3; NPRO 4; NTHZCA 5; NEU 6; MNNG 7; and NMTHZCA 8.

The chemiluminescence detector was considerably more sensitive than the uv detector (FIG. 3). The maximum sensitivity (S/N=3:1) of the detector was less than 1 ng for N-nitrosoamino acids (FIG. 4; 7.5 ng injected) in standard solutions (FIG. 4). N-nitrosamides were somewhat less responsive with limits of detection of approximately 10 ng. These limits are lower than those for volatile N-nitrosamines which typically have thresholds of detection of <0.5 ng injected when analyzed by gas chromatography-TEA. The larger injection volumes used in HPLC compared to gas chromatography more than compensated for the lower sensitivity in the HPLC mode.

The molar response ratios of several N-nitrosoamino acids and N-nitrosamides are given in Table 1. Of the compounds tested, N-nitroso NTHZCA had the highest molar response ratio. N-Nitrosoamides typically had molar response 20 to 50% that of nitrosamines.

TABLE 1

| Solvent | RELATIVE MOLAR RESPONSE RATIOS[a] | | | | | | | | | | | |
|---|---|---|---|---|---|---|---|---|---|---|---|---|
| | N-Nitroso Compound | | | | | | | | | | | |
| % AN[b] | NPRO | NHPRO | NSAR | NPIP | NTHZCA | NMTHZCA | NTMU | MNU | ENU | MNNG | NDMA | NDPA |
| 0 | 1.0 | 1.1 | — | 1.0 | 1.5 | — | 1.0 | 0.8 | — | 1.6 | 0.5 | — |
| 10 | 1.4 | 1.4 | 1.1 | 1.1 | 1.7 | 1.4 | 1.2 | 0.9 | 0.5 | 1.7 | 0.6 | 0.6 |
| 25 | 1.7 | 1.7 | 1.2 | 1.4 | 2.5 | 2.1 | 1.2 | 1.0 | 0.7 | 2.1 | 0.6 | 0.6 |

[a] NPRO (0% AN) = 1
[b] balance 10 - - TFA or water

What is claimed:

1. A photolytic interface positioned between a chromatograph and a detector, for accepting liquid eluate from the chromatograph which contains separated trace amounts of one or more compounds to be detected and analyzed and for converting the said compounds by non-pyrolytic means to a gaseous product to be analyzed with high selectively and sensitivity in said detector which comprises:
   a) a means for combining the liquid eluate from the chromatograph with an inert gas to form a biphasic liquid/gas mixture and for conveying the mixture to a photolytic reactor;
   b) a photolytic reactor for accepting and irradiating the biphasic liquid/gas mixture without pyrolysis to produce a detectable gas product corresponding to the separated trace compounds and for conducting the said gas product in the gas phase to a detector; wherein said reactor is a coiled tube vertically positioned and concentrically disposed around an irradiation means; said coiled tube having a transparent ultraviolet window of from 280 nm to about 430 nm.
   c) a means for regulating the temperature within the reactor below the temperature said compounds would pyrolyze or thermally degrade.

2. The apparatus of claim 1 wherein the reactor tube is a borosilicate glass coil having a length of 10 feet, an inside diameter of about 1 mm and the liquid flow rate is about 1 ml per minute.

3. An apparatus, for measuring the amount of N-nitroso compounds including N-nitrosoamides and non-volatile N-nitrosoamines in a sample wherein N-nitroso compound can be cleaved by UV radiation, which comprises a high performance liquid chromatograph communicating with a liquid/gas interface means capable of converting the sample into nitric oxide (NO) for detection in a detector means interfaced therewith, said liquid/gas interface being a photolytic interface apparatus for accepting liquid eluate from a high-pressure liquid chromatograph which contains separated trace amounts of one or more compounds to be detected and analyzed and for converting the said compounds by non-pyrolytic means to a gaseous nitric oxide (NO) which can be detected and analyzed with high selectivity and sensitivity in a detector which comprises:
   a) a high performance liquid chromatograph to separate trace amounts of the N-nitroso compounds in a sample and deliver a liquid eluate containing the separated compounds to a photolytic interface in communication therewith;
   b) a photolytic interface positioned between the chromatograph and a detector for accepting liquid eluate from the chromatograph, said eluate containing separated trace amounts of one or more compounds to be detected and analyzed, for converting the said compounds by non-pyrolytic means to a gaseous product and conveying said gaseous product to a detector communicating with said interface, wherein said photolytic interface comprises:
      (1) a means for combining the liquid eluate from the chromatograph with an inert gas to form a biphasic liquid/gas mixture and for conveying the mixture to a photolytic reactor;
      (2) a photolytic reactor for accepting and irradiating the biphasic liquid/gas mixture without pyrolysis to produce nitric oxide (NO) gas corresponding to the separated trace compounds and for conveying said gas in the gas phase of the biphasic mixture without reaction with the liquid phase to a detector in communication with said reactor; wherein said reactor is a coiled tube vertically positioned and concentrically disposed around an irradiation means to allow unobstructed continuous flow of liquid/gas mixture assisted by gravity; said coiled tube having a transparent ultraviolet window of from 190 nm to about 430 nm;
      (3) a means for regulating the flow rate of the inert gas and the flow rate of the liquid;
      (4) a means for regulating the temperature of the reactor below the temperature said compounds would pyrolyze or thermally degrade;
   c) a means for separating other components of the liquid/gas mixture exiting the photolytic reactor from the gaseous product to be detected and analyzed;
   d) a detector to detect and analyze the nitric oxide (NO) gaseous product from the separating means.

4. The apparatus of claim 3 wherein the detector is a chemiluminescence detector for detecting nitric oxide (NO).

5. The apparatus of claim 3 wherein the reactor tube is a coiled tube of borosilicate glass transparent to uv radiation at 280 to 430 nm, having an inside tube diameter of from about 0.5 mm to 2.5 mm and an outside diameter of from 3.2 mm to about 6.4 mm.

6. The apparatus of claim 5 wherein the tube has a length of 10 feet, an inside diameter of about 1 mm and a liquid flow rate of about 1 ml per minute.

7. The apparatus of claim 3 wherein said separating means comprises multiple cold traps in series including a first trap at a temperature of 0° C., a second trap at at temperature about −70° C. and a third trap at about −150° C.

* * * * *